United States Patent [19]
Lynch et al.

[11] Patent Number: 5,336,185
[45] Date of Patent: Aug. 9, 1994

[54] PROTECTION DEVICE FOR SYRINGE NEEDLES

[76] Inventors: Richard A. Lynch, 206 Spring St., Cranston, R.I. 02910; William J. Kirk, 327 Gilbert Stuart Dr., East Greenwich, R.I. 02818; Lawrence J. Dario, Nayatt Point, Barrington, R.I. 02806

[21] Appl. No.: 999,106

[22] Filed: Dec. 31, 1992

[51] Int. Cl.⁵ .............................. A61M 5/00
[52] U.S. Cl. ................... 604/110; 604/198; 604/263
[58] Field of Search ............... 604/110, 187, 192, 198, 604/263, 218, 232

[56] References Cited
U.S. PATENT DOCUMENTS

| | | | |
|---|---|---|---|
| 5,045,066 | 9/1991 | Scheuble et al. | 604/198 |
| 5,053,018 | 10/1991 | Talonn et al. | 604/263 X |
| 5,104,386 | 4/1992 | Alzain | 604/232 |
| 5,201,721 | 4/1993 | Lee et al. | 604/198 |

*Primary Examiner*—John D. Yasko
*Attorney, Agent, or Firm*—Robert J. Doherty

[57] ABSTRACT

A safety device for use with standard or dental syringes as an add-on feature or as a retrofit in which a safety sleeve moves over the normally exposed front end of a needle to protect users from being accidentally stuck.

18 Claims, 5 Drawing Sheets

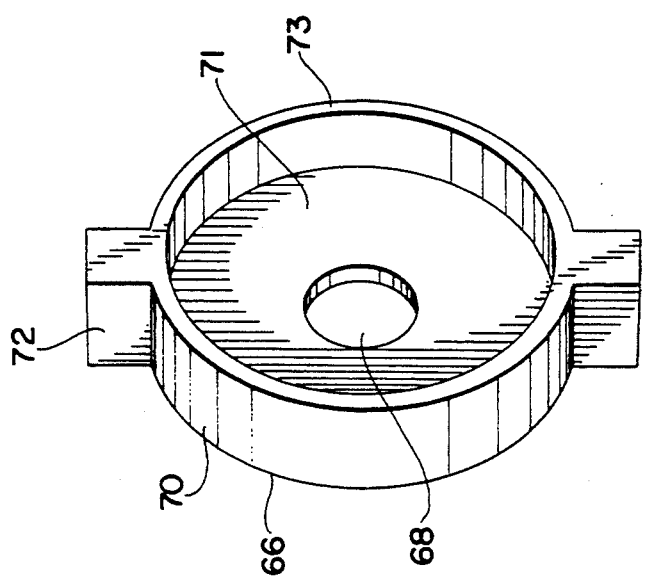
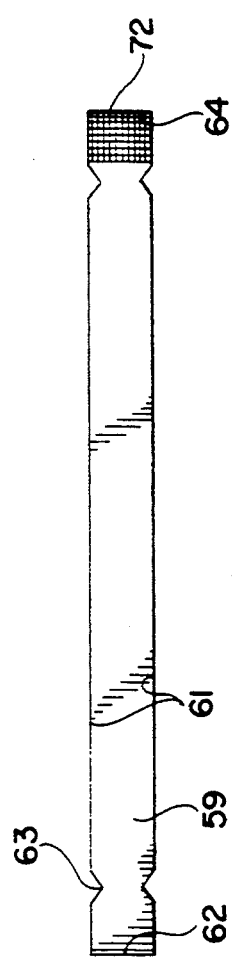
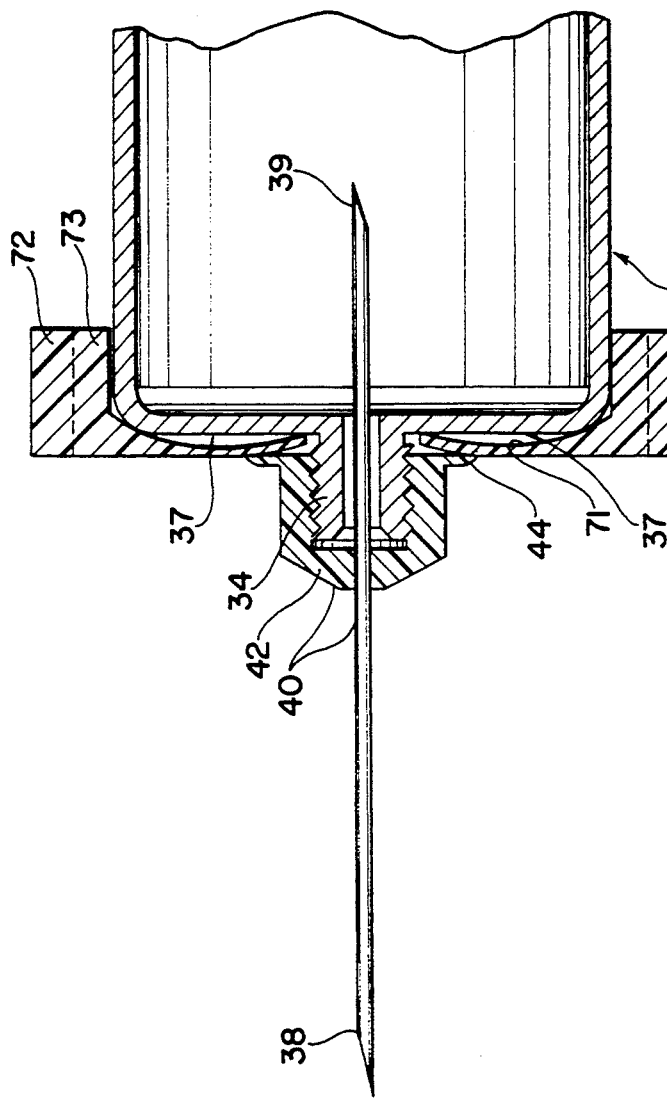
FIG. 5
FIG. 2a
FIG. 4

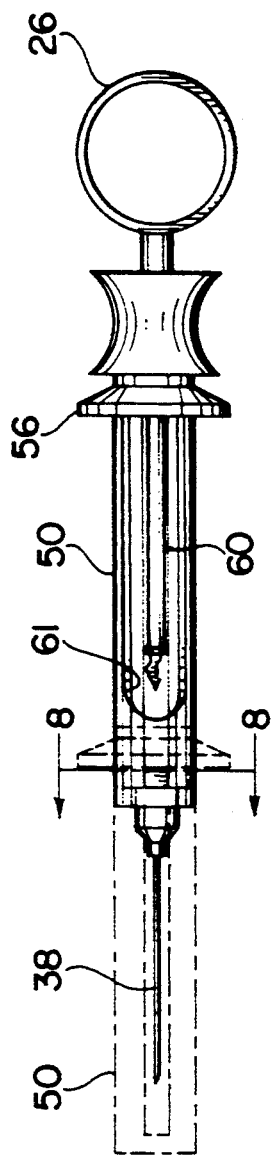
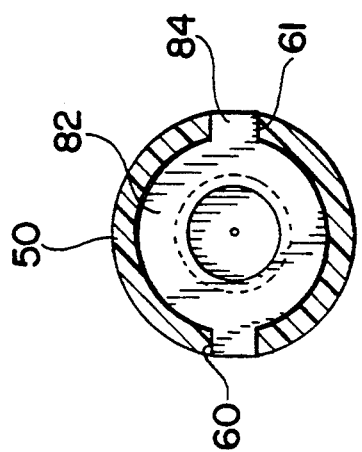
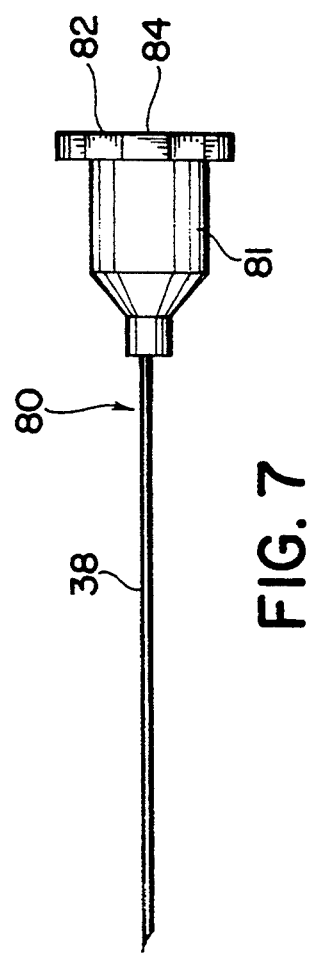

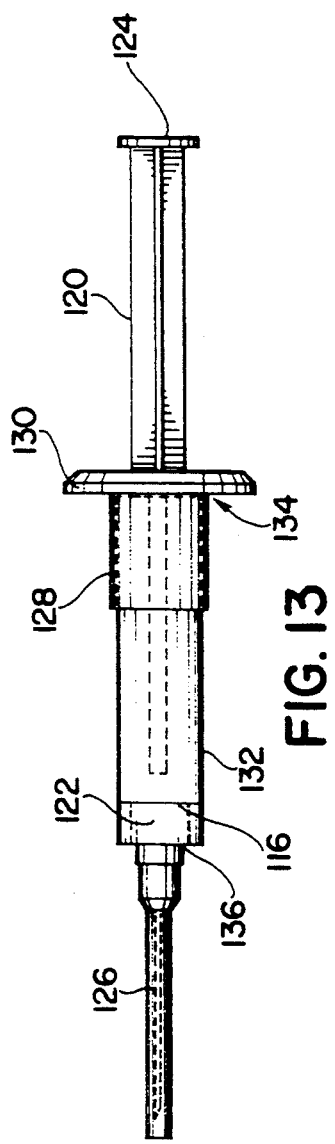
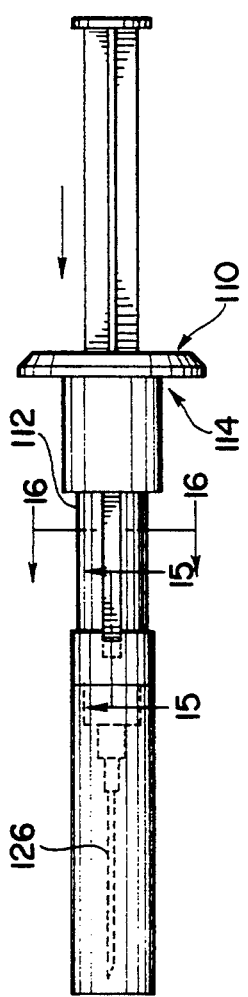
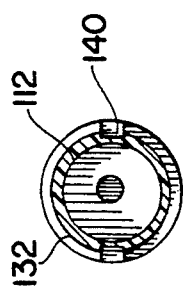
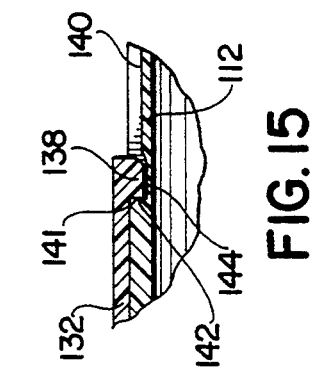
FIG. 13
FIG. 14
FIG. 15
FIG. 16

PROTECTION DEVICE FOR SYRINGE NEEDLES

BACKGROUND AND OBJECTS OF THE INVENTION

This invention relates to both general purpose and special purpose syringes in which an attached needle assembly is exposed during use. Since concern for blood borne diseases is particularly acute today, various procedures have been proposed to lessen or eliminate the chances for the needle to accidentally stick those using the syringe during various medical procedures in which the syringe is passed back and forth as between a doctor/nurse and assistants. The same general concerns relate to both standard hypodermic needle syringes for general use as well as syringes particularly designed for dental use.

Specifically in regard to dental use, the current practice for injecting a local anesthetic into a patient and the subsequent handling of the needle is as follows:

The dental assistant screws a needle into the sterilized syringe. The needle used is double ended. i.e., a "long" end which is inserted into the patient and a "short" end which is forced through a membrane, i.e., a surgical rubber plug, and into a cartridge containing local anesthetic. The hub of the needle can be plastic or aluminum. Both ends of the needle are capped. The assistant removes the cap from the short end of the needle and screws it onto the threaded end of the syringe.

The assistant then inserts a cartridge containing the local anesthetic into the syringe. The plunger is spring loaded and by pulling out on the plunger, sufficient space is made to insert the cartridge. When the plunger is released, the short end of the needle pierces the membrane in the bottom of the cartridge allowing the local anesthetic to be released when pressure is applied to the plunger. The syringe is now ready for use. The cap on the long end of the needle is removed exposing the needle. The dentist can now make the stick.

After the stick is made, one of two things can happen: 1) no more injections are needed for this patient, and the needle must be thrown away; or b) additional injections are needed and then the needle is thrown away. If this specific patient is to have further injections, then the needle is recapped, handed to the assistant (or handed to the assistant and then recapped) so that a new cartridge can be inserted into the syringe. The same procedures as outlined above are followed. In some cases, the dentist can forget to recap the needle and will leave the exposed needle on the work surface.

Once the new cartridge is inserted, the syringe is now handed back to the dentist and the cap removed (or the cap is removed and then handed back to the dentist). The new stick can now be made.

Once all sticks are done, the needle must now be removed and disposed of in the sharp container. The first step is to recap the needle. Once recapped by the dentist, the syringe is handed to the assistant (or it is handed to the assistant and then recapped).

It thus can be seen that extensive needle exposure is present in this system and the passing back and forth of such devices could easily result in accidental sticks. However, there is widespread use of this system, and it is popular. Accordingly, it would be desirable to provide a device which reduces exposure to accidental sticks yet continues to utilize this general system.

Similarly with respect to a standard hypodermic needle, the uncapped point thereof is exposed during passage between doctors and assistants in a similar fashion; and, accordingly, it would also be desirable to provide a device which reduces such exposure to accidental sticks with respect to standard hypodermic needle syringes as well.

These and other objects of the present invention are accomplished by the provision of a device for the safe handling of hypodermic syringes of the type having a hollow cylindrical body for containing fluids with opposed forward and rear ends with a needle assembly mounted at said forward end and including a forwardly projecting normally exposed needle, and an injection assembly mounted at said rear end and including a hand-manipulatable, longitudinally-movable piston for injecting fluid housed in said body through said needle and into a patient, said device including a tubular safety sleeve having an inner diameter slightly larger than that of the hollow cylindrical body of the syringe and adapted for telescopic mounting over said body and further adapted for back and forth forward to rearward sliding movement therein from a full rearward position wherein said needle is exposed to a full forward position wherein said needle is housed within the confines of said sleeve and thus protected from coming in contact with users or patients and means associated with said safety sleeve for limiting the forward and rearward motion of said sleeve vis-a-vis said syringe.

Other objects, features and advantages of the invention shall become apparent as the description thereof proceeds when considered in connection with the accompanying illustrative drawings.

DESCRIPTION OF THE DRAWINGS

In the drawings which illustrate the best mode presently contemplated for carrying out the present invention:

FIG. 2a is a detail of the longitudinal slot 60 in the safety sleeve barrel 50 showing an option that will enable the sleeve to latch at the extreme ends of travel;

FIG. 4 is a partial sectional view taken along the line 4—4 of FIG. 3;

FIG. 5 is a perspective view of a preferred form of the plug or disc shown in the embodiment illustrated in FIGS. 1-4;

FIG. 6 is a an elevational view of a further embodiment of the present invention in which an alternate means is utilized to guide the safety sleeve back and forth along the outer body or barrel of a dental hypodermic syringe;

FIG. 7 is an enlarged elevational view of the modified needle construction shown in FIG. 6;

FIG. 8 is an sectional view of taken along the line 8—8 of FIG. 7;

FIG. 13 is a an elevational view similar to FIG. 1 but showing the safety sleeve construction of the present invention associated with a standard hypodermic needle syringe;

FIG. 14 is a view similar to FIG. 13 but showing the syringe in its fully expanded position and with the safety sleeve positioned in its forward most needle protective attitude;

FIG. 15 is a partial sectional view along the line 15—15 of FIG. 14; and

FIG. 16 is a sectional view along the line 16—16 of FIG. 14.

DETAILED DESCRIPTION OF THE INVENTION

Figure 1:
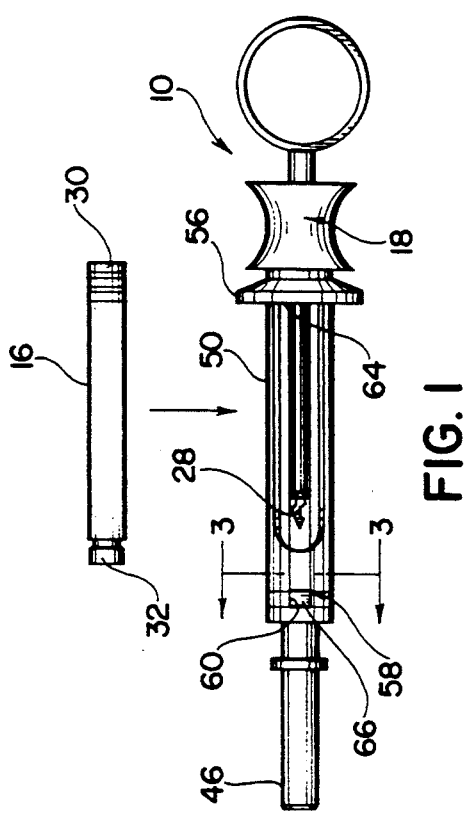
FIG. 1 is an elevational assembly view of one form of the present invention utilized in conjunction with a standard dental hypodermic syringe.
Figure 2:
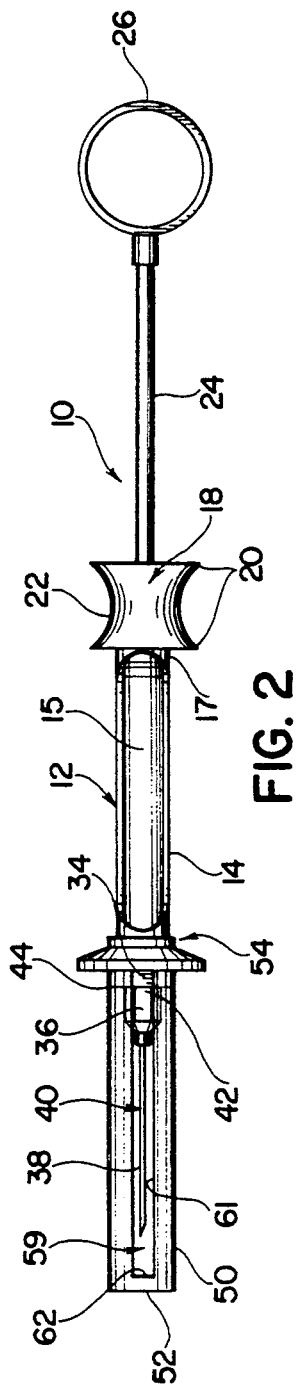
FIG. 2 is a view similar to FIG. 1 showing the device of FIG. 1 in a ready position and with the safety sleeve of the present invention in a forward position to protect the uncapped needle housed therein.
Figure 3:
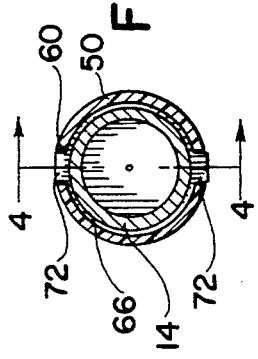
FIG. 3 is a sectional view taken along the line 3—3 of FIG. 1.
Figure 10:
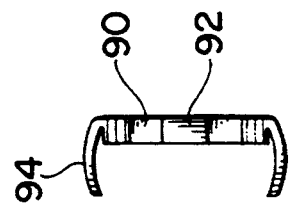
FIG. 10 is a side elevational view of FIG. 9 with parts removed for clarity.

Turning now to the drawings and particularly FIGS. 1 through 3 thereof, a standard dental hypodermic syringe is depicted. Such dental syringe 10 includes a body 12 including a cylindrical barrel 14 which includes a cut away window 15 to receive disposable cartridges 16. The barrel as well as the remaining syringe body portions are preferably formed of stainless steel or some other metal that can be repeatedly utilized and sterilized without ill effect.

The body base 17 includes a stem or grasping portion 18 having spaced flanges 20 joined by a rounded depressed area 22. A plunger 24 is mounted in the stem 18 and is prevented from complete withdrawal therefrom by known stop means, The plunger 24 further includes a finger ring 26 by which the plunger can be manipulated in the intended manner. The end of the plunger 24 includes a piercing dart 28 such that the base 30 of the cartridge 16 can be pierced. The opposite end of the cartridge 16 includes a rubber cap 32 inn which the short end 39 of a double needle 36 is adapted to pierce. The larger forward needle end 38 projects forwardly in the intended manner, and the needle assembly 40 further includes a hub 42 formed from plastic or metal which further may include a short outwardly extending flange 44. The needle hub is threaded onto a threaded stem 34 which forwardly projects from the terminal shoulder surface 37 at the front of the barrel 14. A safety cover 46 is adapted to extend over the needle. Such cover may be threaded or frictionally held by the hub 42 outer surface.

A safety sleeve 50 basically of cylindrical construction having a forward end 52 and a rear end 54 is positioned over the barrel as shown. The sleeve 50 is adapted to extend over the outside surface of the barrel 14 and move back and forth thereon to alternately cover the exposed needle 38 in its most forward position as shown in FIG. 2 and be retracted in the position as shown in FIG. 1 such that the needle when the cover 46 is removed therefrom can be utilized to administer fluids such as a Novacaine or Lidocaine to a dental patient. The rear end 54 of the sleeve 50 is preferably provided with an outwardly extending radial flange 56 for convenience in one-handedly moving the sleeve 50 forward and returning the same as by the user's thumb. Generally, the sleeve is formed of plastic and is of one piece injection molded construction.

A combination stop and guide means 59 is associated with the sleeve 50. Such in part takes the form of preferably a pair of opposed longitudinally directed slots 60 extending through the body of the sleeve terminating in ledges 62 and 64 at forward and rear ends thereof respectively. Each slot includes opposed edges 61. A plug in the form of a radial disc 66 is mounted at the forward end of the barrel 14. Such disc 66 includes a central opening 68 such that it may be mounted over the forwardly projecting threaded stem 34 on which the needle is attached and a body 70 generally co-extensive with the barrel 14. The disc includes a pair of outwardly extending radial ears 72. The width of the slots 60 is such that the ears 72 extend there into and frictionally contact the opposed edges 61 of the slots 60. As may be apparent, the ledge 62 contacts forward portions of the ears 72 to limit the rearward motion of the safety sleeve 50, and the ledge 64 contacts rearward portions of the ears in the forward position of the sleeve to limit the forward motion thereof. In this manner then, the forward and rear limits of the sleeve travel vis-a-vis the barrel 14 can be determined.

Another way of accomplishing such is by narrowing the width of the slots at the opposed terminal ends thereof such that higher frictional contact is accomplished proximal to the ends thereof by means of the constant width of the ears. In this way then increased frictional resistance determines the point at which the forward and rearward limits of the sleeve are brought about rather than a potentially more positive stop contact between the edges and ears surfaces. Also as shown in FIG. 2A, the slot itself may include means by which locking of the ear or ears at one or both ends is achieved. Indentations 63 are thus provided on the edges of slot 59 such that the ears contact such indentations with increased frictional contact so as to in effect lock the barrel 50 in place.

Generally, however by making the sleeve of plastic resinous material such as a somewhat rigid polyethylene and by making the slot width equal to or slightly narrower than the thickness of the ears, a desired friction can be achieved. Thus in these cases, the plastic structure allows some give or widening in central sections of the slots and little or none at the ends so that an increased friction is felt by the user as the sleeve approaches either end.

As can be best seen from FIGS. 4 and 5, the disc 66 in this embodiment preferably includes a body 70 which includes a hollowed out interior 71 such that the ears 72, in effect, extend partially radially outward from flanges 73 formed by such hollowed out interior. Generally, the disc 66, by reason that its ears 72 are protrude into slots 60 of sleeve 50, rotates as a unit with the sleeve. Thus if the sleeve is inadvertently or purposely rotated during use, the disc rotates with respect to the syringe barrel 14 and the needle assembly attached thereto. Note that when the hub 42 of the needle 36 presses downwardly against the disc 66, it tends to downwardly bend those portions of the disc adjacent the opening 68 downwardly so only a low frictional contact in the form of a circular line contact between the hub and the disc preferably occurs. This means that rotational movement of the disc 66 along with the sleeve 50 tends not to move the needle with respect to its stem attachment since the friction imparted thereto is only slight and the friction of the threads on the syringe barrel 34 and the needle hub 42 is far greater. Thus, the needle 36 does not tend to undesirably unscrew vis-a-vis the syringe. Also, the material from which the disk is made can alter the frictional characteristics so as to either decrease or increase the friction at the needle hub-disk interface.

If it is undesirable to have the sleeve 50 rotate with respect to the syringe, then the interior portions 71 of the disc 66 can be roughened or textured to increase frictional resistance or reshaped, i.e., flattened, to assure greater contact with the shoulder 36. In some cases, it may, however, be desirable to be able to unscrew the needle by rotating the sleeve and such will be discussed hereinafter with respect to the embodiments shown in FIGS. 6–12.

Your attention is now directed to FIG. 6 of the drawings wherein an alternate combination stop and guide means is utilized. Therein a modified needle assembly 80 is utilized in which the hub 81 includes an enlarged flange 82 from which in turn the integral ears 84 extend. The body may be similar in construction to the body 70 of disc 66 except that it is formed from the base of the needle assembly 80 and integral therewith. Obviously when using the needle assembly 80, the separate disc 66 is not required. Thus instead of, in effect, trapping the plug or disc 66 between the needle assembly and the shoulder 37, a modified needle assembly which includes an integral disc is substituted for the separate disc. Naturally, this requires a custom needle construction.

Further alternate embodiments in which separate modified forms of the disc 66 can be utilized are shown in FIGS. 9–12. Specifically referring to FIGS. 9 and 10, one form of such alternate disc 66 is shown in which disc 66a has a body 90 with a pair of outwardly radially extending ears 92 for which the slots 60 of the sleeve 50 are adapted to move back and forth on and a pair of protruding webs or flaps 94 integral with the body 90 and outwardly radially extending therefrom and which act as friction brakes on the inside of the sleeve 50. These flaps extend upwardly a short distance and then forwardly and are preferably formed of a plastic material such as polyethylene and molded in the depicted position such that they tend to be inwardly radially deflected by the movement of the sleeve thereacross. In that regard, the outside diameter of this alternate form of disc 66 is preferably dimensioned to be slightly greater than the inside diameter of the sleeve 60.

Figure 12:
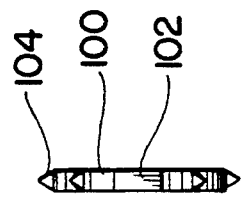
FIG. 12 is a side elevational view of FIG. 11.
Figure 9:
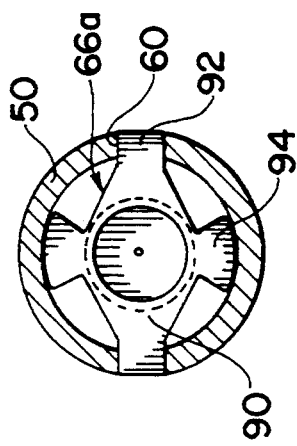
FIG. 9 is a view similar to FIG. 8 but showing a modified form of the friction disc.
Figure 11:
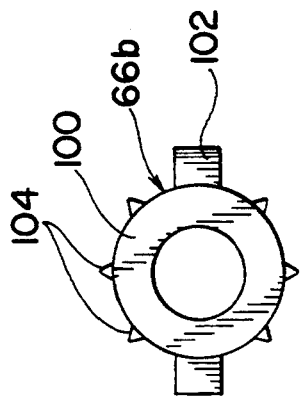
FIG. 11 is a view similar to FIG. 9 showing still another modified form of the friction disc with parts removed for clarity.

A further form of such alternate disc construction is shown in FIGS. 11 and 12 in which a disc 66b includes a pair of ears 102 adapted to extend into the slots 60 as previously indicated as well as a body 100 on which a plurality of radially extending barbs 104 are provided. Such barbs 104 are dimensioned so as to form a tip to tip diameter slightly greater than that of the inside diameter of the sleeve 50 such that the above described friction braking therebetween is accomplished. Such disc 66a and 66b should be formed from a flexible polymeric material such as low density polyethylene and preferably should match the color of the sleeve 50.

With the above-modified forms of the invention shown in FIGS. 6–12, rotational movement of the sleeve 50 vis-a-vis the syringe barrel 14, of course, causes movement of the respective needle assembly. Thus by rotating the sleeve counter-clockwise, the needle assembly can be unscrewed from the stem 34. This may in some cases be an advantage for the removal and disposal of needles especially dangerous double-ended needles. Such action would most advantageously be done with the sleeve in the full forward position and when the needle is fully detached from the stem, the whole unit could be simply opened to let the needle drop through the open sleeve end into a disposal safe. Also in some cases, although generally not practical, the special forms of the disc shown in FIGS. 9–12 could be incorporated into the needle assembly hub of the FIGS. 6–8 embodiments.

Operation of the device of the present invention in the forms above described is as follows:

In the injection mode, the sleeve is positioned up over the barrel of the syringe covering the cartridge. This exposes the needle for normal use. Once the injection is made, the safety sleeve is slid down over the needle thereby covering up the needle. In this protect position, it is difficult to have an accidental needle stick unless the operator sticks their finger up into the sleeve and the needle. Only very small fingers can be inserted into the sleeve far enough to reach the needle. The safety sleeve is installed together with the new needle. It is fed over the threaded portion of the syringe and held in position by the hub of the needle. When the needle is removed, the safety sleeve is also removed and thrown away. With the safety sleeve in the protect position and the needle removed from the syringe, both ends of the needle are covered up. It should not be re-used since infected body fluids could be dripped from the needle onto the sleeve, or contamination from the hands of the person doing the stick, or direct physical contact with the patient could pass infectious material to the sleeve.

Thus some of the safety features of the present invention in the form above illustrated include:

the use of a one-handed operation and should meet the latest OSHA standards;

covers the needle when not in use thereby reducing the possibility of accidental needle sticks;

covers both ends of the needle when removed from the syringe and in the protect position;

very inexpensive; and disposable.

Turning again to the drawings and particularly FIGS. 13 through 16 thereof, the safety device of the present invention is shown in conjunction with a standard hypodermic syringe 110 and needle. Such hypodermic syringe 110 includes a body 112 of cylindrical construction having rear and forward ends 114 and 116 respectively. The body 112 is fitted with a standard plunger 118 having a shaft 120, a forwardly mounted piston 122 and a rear flattened head or push surface 124 such that the piston can be forwardly pushed to inject fluid into a patient via the standard associated needle construction 126 and withdrawn as by grasping such. In order to enable the flattened head to be more easily grasped between the user's finger and thumb while holding the body 112, a shortened forwardly extending cylindrical boss 128 is provided at the rear end 116 of the body 112. Such boss 128 is integral with the end hold flange 130 and of a diameter slightly greater than that of the body 112 such that a safety sleeve 132 may be positioned therein as best shown in FIG. 14.

The safety sleeve 132 includes a rear end 134 and a forward end 136 and further includes a pair of radially inwardly extending fingers 138 at the rear end 136 thereof. Such fingers are adapted to extend into grooves longitudinally extending into the surface of the body 112. The grooves 140 terminate at their forward end in a stop surface 142 which is adapted to contact a forward surface 141 similarly provided on the fingers 138. Such grooves 140 may also preferably be provided at their forward ends with increased depth pockets 144 such that the fingers when approaching such will tend to snap there-into and provide a positive feel to the intended forward sleeve travel vis-a-vis the body 112. The operation of the sleeve with respect to the use of the otherwise standard hypodermic needle shown in FIGS. 4 through 7 is as previously explained with reference to the embodiments shown in the previous drawings.

While there is shown and described herein certain specific structure embodying this invention, it will be manifest to those skilled in the art that various modifications and rearrangements of the parts may be made without departing from the spirit and scope of the underlying inventive concept and that the same is not limited to the particular forms herein shown and described except insofar as indicated by the scope of the appended claims.

What is claimed is:

1. A device for the safe handling of hypodermic syringes of the type having a hollow cylindrical body with opposed forward and rear ends with a needle assembly mounted at said forward end and including a forwardly projecting normally exposed needle, and an injection assembly mounted at said rear end and including a hand-manipulatable, longitudinally-movable piston for injecting fluid housed in said body through said needle and into a patient, said device including a tubular safety sleeve having an inner diameter slightly larger than that of the hollow cylindrical body of the syringe and adapted for telescopic mounting over said body and further adapted for back and forth forward to rearward sliding movement therein from a full rearward position wherein said needle is exposed to a full forward position wherein said needle is housed within the confines of said sleeve and thus protected from coming in contact with users or patients and means associated with said safety sleeve for limiting the forward and rearward motion of said sleeve vis-a-vis said syringe, said means for limiting the forward movement of said sleeve being a stop means positioned at the forward end of said body which in turn contacts rear portions of said sleeve to prevent further forward movement of said sleeve, said sleeve including a longitudinally oriented guide slot in which disc means are mounted at the forward end thereof for frictional contact therewith, said disc means including a body having a central hole and at least one ear radially projecting into said slot so as to guide said sleeve's movement over said cylindrical body, and means for positioning the disc means longitudinally stationary with respect to the forward end of said body, said means for positioning said disc body including a threaded stem forwardly extending from said body into the hole of said disc and a needle assembly having a threaded base to accept said stem, said disc body being separate from said syringe body and said needle assembly.

2. The device of claim 1, said needle assembly base having an outwardly radially projecting flange adapted to contact said disc.

3. The device of claim 1, said syringe being a standard dental syringe.

4. The device of claim 1, said slot in said sleeve terminating at the rear end thereof short of the rear terminus of the sleeve so as to form a ledge, said ledge adapted to contact said ear in the forward most movement of said sleeve vis-a-vis said body.

5. The device of claim 4, there being a pair of guide slots formed in said sleeve at opposite sides thereof.

6. The device of claim 1, said disc body including a hollowed out lower interior portion such that the overall configuration of said body is that of a cylindrical cap having outer flanges from which said ears extend.

7. The device of claim 1, said disc body held by said syringe forward body end and said needle assembly from longitudinal movement but free for at least partial rotational movement with respect to said syringe body along with said sleeve, said sleeve and disc body moving as a unit rotationally but separate with respect to longitudinal movement.

8. The device of claim 1, said disc body being a part of said needle assembly.

9. The device of claim 8, said needle assembly needle having a lower hub adapted for threaded attachment to said syringe body, said ears being an integral part of said hub.

10. The device of claim 1, said disc means including secondary means to regulate the frictional contact between said disc body and interior surfaces of said sleeve.

11. The device of claim 10, said secondary means being a pair of flaps integrally molded with said disc body and longitudinally extending therefrom and in contact with said sleeve inner surfaces.

12. The device of claim 10, said secondary means being a plurality circumferentially-spaced barbs radially outwardly extending from said disc body and in contact with said sleeve inner surfaces.

13. The device of claim 1, said slot means including a longitudinally oriented guide groove positioned in said body on the outside surface thereof and terminating in a ledge at the forward end thereof, said sleeve in turn having a radially inwardly extending lug mounted at its rear portion and adapted to engage said groove during said back and forth movement and further to contact said ledge at the full forward position of said sleeve with respect to said body.

14. The device of claim 13, said groove further including an increased depth recess proximal said forward ledge for snap lock receipt of said lug.

15. The device of claim 14, there being a pair of guide grooves on said body and a pair of cooperating lugs on said sleeve.

16. The device of claim 14, there being a pair increased depth recess proximal the rear portion of said groove for engaging said boss at its' rearward extent of travel with respect to said body.

17. The device of claim 13, said syringe body including a short forwardly extending cylindrical boss positioned at its rear portion, said boss concentric with said body and having a diameter slightly larger than said body so as to enable rear portions of said sleeve to extend between said body and said boss and thereby enable the device to be gripped by a user by contacting outer portions of said boss rather than said slideable sleeve.

18. A device for the safe handling of hypodermic syringes of the type having a hollow cylindrical body with opposed forward and rear ends with a needle assembly mounted at said forward end and including a forwardly projecting normally exposed needle, and an injection assembly mounted at said rear end and including a hand-manipulatable, longitudinally-movable piston for injecting fluid housed in said body through said needle and into a patient, said device including a tubular safety sleeve having an inner diameter slightly larger than that of the hollow cylindrical body of the syringe and adapted for telescopic mounting over said body and further adapted for back and forth forward to rearward sliding movement therein from a full rearward position wherein said needle is exposed to a full forward position wherein said needle is housed within the confines of said sleeve and thus protected from coming in contact with users or patients and means associated with said safety sleeve for limiting the forward and rearward motion of said sleeve vis-a-vis said syringe, said means for limiting the forward movement of said sleeve being a stop means positioned at the forward end of said body which in turn contacts rear portions of said sleeve to prevent further forward movement of said sleeve, said sleeve including a longitudinally oriented guide slot in which disc means are mounted at the forward end thereof for frictional contact therewith, said disc means including at least one ear radially projecting into said slot so as to guide said sleeve's movement over said cylindrical body, and means for positioning the disc means longitudinally stationary with respect to the forward end of said body, said means for positioning said disc body including a threaded stem forwardly extending from said body into the hole of said disc and a needle assembly having a threaded base to accept said stem, said disc body including a hollowed out lower interior portion such that the overall configuration of said body is that of a cylindrical cap having outer flanges from which said ears extend, said interior portions adjacent to said opening adapted to be downwardly bent against said forward end of said syringe body by the threaded end of said needle base.

* * * * *